US008000501B2

(12) United States Patent
Huotilainen

(10) Patent No.: US 8,000,501 B2
(45) Date of Patent: Aug. 16, 2011

(54) METHOD AND PRODUCT FOR DETECTING ABNORMALITIES

(75) Inventor: Tommi Huotilainen, Helsinki (FI)

(73) Assignee: ABB Oy, Helsinki (FI)

( * ) Notice: Subject to any disclaimer, the term of this patent is extended or adjusted under 35 U.S.C. 154(b) by 839 days.

(21) Appl. No.: 11/921,226

(22) PCT Filed: Jun. 22, 2006

(86) PCT No.: PCT/FI2006/000223
§ 371 (c)(1),
(2), (4) Date: Jan. 17, 2008

(87) PCT Pub. No.: WO2007/003685
PCT Pub. Date: Jan. 11, 2007

(65) Prior Publication Data
US 2009/0022391 A1  Jan. 22, 2009

(30) Foreign Application Priority Data

Jul. 1, 2005  (FI) ..................................... 20050706

(51) Int. Cl.
*G06K 9/00* (2006.01)
*G06F 19/00* (2011.01)
(52) U.S. Cl. .......................... 382/108; 382/149; 700/122
(58) Field of Classification Search .................. 382/100, 382/141, 143, 149, 151, 162, 168, 173, 181, 382/193, 194, 199, 219, 232, 254, 260, 274, 382/276, 284, 286–295, 305, 312, 321; 702/40; 700/122
See application file for complete search history.

(56) References Cited

U.S. PATENT DOCUMENTS

| 5,068,799 | A  | * | 11/1991 | Jarrett, Jr. ....................... 702/40 |
| 6,466,700 | B1 |   | 10/2002 | Makram-Ebeid |
| 6,728,592 | B2 | * | 4/2004  | Wells ............................. 700/122 |
| 6,990,255 | B2 | * | 1/2006  | Romanik et al. ............... 382/284 |
| 7,817,844 | B2 | * | 10/2010 | Kitamura et al. .............. 382/141 |
| 2002/0054293 | A1 |   | 5/2002 | Pang et al. |
| 2002/0109112 | A1 |   | 8/2002 | Guha et al. |
| 2002/0154810 | A1 | * | 10/2002 | Hakim et al. .................. 382/149 |
| 2003/0053713 | A1 |   | 3/2003 | Romanik et al. |

(Continued)

FOREIGN PATENT DOCUMENTS
EP   0 742 431 A1   11/1996
(Continued)

OTHER PUBLICATIONS
*Kevin Erler et al., "Adaptive Recursive Image Filtering", IEEE, US, vol. 2 Conf. 16, Apr. 14, 1991, pp. 3017-3020.

(Continued)

*Primary Examiner* — Seyed Azarian
(74) *Attorney, Agent, or Firm* — Buchanan Ingersoll & Rooney PC

(57) ABSTRACT

A new method for processing image data in order to detect abnormalities in a web is provided. The web is monitored by at least one camera, whereby an image comprising of plurality of pixels is generated. The data of the image is stored in a memory. Image data is filtered by a processor by creating a filtered image data by weighting the image data and at least one of earlier image data and earlier filtered image data; and combining the weighted image data and at least one of the weighted earlier image data and the weighted earlier filtered image data; and controlling filtering by at least one nonlinear algorithm; and thresholding the created filtered image data.

29 Claims, 5 Drawing Sheets

U.S. PATENT DOCUMENTS

2005/0135667 A1 * 6/2005 Saarela et al. ............... 382/141

FOREIGN PATENT DOCUMENTS

| EP | 0 816 825 A2 | 1/1998 |
| EP | 1 107 181 A2 | 6/2001 |

OTHER PUBLICATIONS

*PCT/ISA/210, (2005).
*Finnish Search Report.
*PCT/IPEA/409, (2005).

* cited by examiner

METHOD AND PRODUCT FOR DETECTING ABNORMALITIES

TECHNICAL FIELD

The present invention relates to a method for processing image data in order to detect abnormalities in a web and to a computer program product stored on computer operable media for processing image data in order to detect abnormalities in a web.

BACKGROUND ART

Web inspection systems utilize today imaging techniques for detecting defects and other anomalies. Holes, spots and dirt particles are examples of defects and wrinkles, streaks and slime spots are examples of weak defects to be detected for paper makers. Correspondingly, for sheet-metal makers, slag inclusions, cracks and scratches are examples of defects and weak cracks, weak scratches and indentations are examples of weak defects to be detected. In these cases, the weak defect causes only a slight change to the intensity level of the digital video signal compared to the mean variation of the signal measured from a faultless product.

Currently weak, elongated defects on a web are best detected by averaging or integrating methods. The optimal result is found only when the defect runs exactly in the cross direction of the web, the defect runs exactly in the machine direction of the web, or the defect runs in some exact angle direction of the web product.

Matching filters or two-dimensional Finite Impulse Response (FIR) filters (for example edge operators) are utilized for the detection of weak defects, but the amount of defect sizes and shapes is limited. For instance in US 2002054293 A1 is described how to find optimal matching filters for textured materials.

The traditional way to detect streaks is to integrate or average the video signal in machine direction in order to improve the Signal-to-Noise (S/N) ratio. For increased cross-directional resolutions of digital cameras and high demands for detecting weaker streaks, the traditional method is not adequate. As high cross-directional resolutions are used, the number of cross-directional pixel positions is high and the width of one pixel is small. This may lead to problems in the traditional method for example due to normal oscillations of the machinery, since the web and thus also the streak may oscillate and a narrow streak may move away from its original cross-directional pixel position. Thus, simple averaging or integration in the machine direction is not optimal for streak detection. The streak detection method should be capable of following the streak whenever the cross-directional position changes slightly.

There is a need for a detection method capable of handling defects including weak defects.

DISCLOSURE OF THE INVENTION

The purpose of this invention is to solve the above problems and to create a new method for processing image data in order to detect abnormalities in a web, wherein the web is monitored by at least one camera, whereby at least one image comprising of plurality of pixels is generated for creating the image data, and the image data is stored in a memory, the image data is filtered by a processor for creating a filtered image data by weighting the image data and at least one of earlier image data and earlier filtered image data; and combining the weighted image data and at least one of the weighted earlier image data and the weighted earlier filtered image data; and controlling the filtering by at least one nonlinear algorithm; and thresholding the created filtered image data.

The second aspect of the invention is to create a computer program product stored on computer operable media for processing image data in order to detect abnormalities in a web, wherein the web is monitored by at least one camera, whereby at least one image comprising of plurality of pixels is generated for creating the image data, and the image data is stored in a memory, wherein the computer program product comprises: means for filtering the image data by a processor, means for creating a filtered image data by weighting the image data and at least one of earlier image data and earlier filtered image data; and means for combining the weighted image data and at least one of the weighted earlier image data and the weighted earlier filtered image data; and means for controlling the filtering by at least one nonlinear algorithm; and means for thresholding the created filtered image data.

This invention is a local processing method which relies on the idea of the adaptive neighborhood. In the method one or several filters are used together with a nonlinear adaptive algorithm to form a decision-based filter. The filter structure inside the decision-based filter can be for instance an Infinite Impulse Response (IIR) filter or a Finite Impulse Response (FIR) filter. When two or more filters are used in series or in parallel or in matrix, the filters can comprise of different types of filters. Typical examples of nonlinear functions utilized inside the adaptive algorithm are minimum, maximum and median functions.

The adaptive algorithm is used to make a decision on how the earlier image data and/or earlier filtered image data in the local neighborhood of the image data and/or filtered image data are weighted to create a filtered image data value. The weighting of the filtering can be based on several information sources: 1. the earlier image data in the local neighborhood of the current pixel, 2. the earlier filtered image data in the local neighborhood of the current pixel, 3. optional parameters, which can be based on some a priori information and for example force some weights to be fixed to some predetermined value, 4. optional side information data from the previous stage of the filtering process synchronized with the corresponding filter responses and stored in a memory, which lies inside the nonlinear adaptive algorithm structure, 5. optional side information data from another filter of the sequential and/or parallel and/or matrix filter structure. The weighting of the signals used for creating a filtered image data defines the local neighborhood of the image data and the local neighborhood of the filtered image data. Local neighborhood can be defined by earlier image data (forward part of the decision based filter) and/or earlier filtered image data (feedback part of the decision based filter). Depending on the weighting, some defect signal values in a specific direction of the web, in the local neighbourhood of the image data value, can be accentuated. For instance, the earlier image data and/or the earlier filtered image data is weighted from any angle of 0 or 45 or 90 or 135 of the image data and/or the filtered image data.

The side information data can for example include a local angle, a global angle, an angle area, an emphasis angle of the earlier image data and/or the earlier filtered image data, an increasing or a decreasing intensity, a fixed direction, color (for example true or false color), a phase of the angle and some a priori information.

In a special case, all weights but one can also be set to zero to form a selector. The weighting of the earlier image data and/or earlier filtered image data, i.e. which of the multitude of earlier image data values and/or earlier filtered image data values are selected to be combined with the image data, is based on the earlier image data and/or earlier filtered image data or the optional side information of previous filtering processes or the optional parameters.

Side information data can be created based on:

the earlier image data and/or earlier filtered image data; or the side information data of previous filtering processes; or one or several parameters; or the side information data of previous filter.

The side information data can also be fixed to a predetermined value. The side information data is stored in a memory, which lies inside the adaptive algorithm structure.

One principle of the method is to utilize minimum and maximum functions inside the adaptive algorithm, and to form a method where the maximum intensity ridges or the minimum intensity valleys in the source video signal are followed and integrated or averaged in the direction of the ridge or the valley. The invention can also be utilized for weak area detection, where a weak area can be considered as a short and wide curve. The method integrates the signals in the highlands or in the lowlands of the weak areas. The strength of the method is based on the ability of spreading out over a weak area regardless of the shape or the size of the area.

In this invention, the detection can be parametrized to cover defects with any angles between 0-180° at the same time. In practise, 0° refers to cross direction of the web and 90° to machine direction. However, the image data can be processed in any direction within the angle range. If, for instance, a preprocessing method rotates the image 45° then 0° in the calculation is 45° in reality and 90° in the calculation is 135° in reality.

The defect detection can be focused to a sector of permitted emphasis angles. The earlier image data and/or the earlier filtered image data is weighted in an emphasis angle. The permitted emphasis angles of the earlier image data and/or earlier filtered image data for creating the filtered image data can be for instance fixed to a predetermined sector; or the same as the previous sector of permitted emphasis angles of the earlier image data and/or earlier filtered image data; or limited to a more narrow sector or expanded to a wider sector compared to the previous sector of permitted emphasis angles of the earlier image data and/or earlier filtered image data; or independent on the previous emphasis angle of the earlier image data and/or earlier filtered image data; or be dependent on the previous emphasis angle of the earlier image data and/or earlier filtered image data; or be adjusted automatically based on the detection result of for instance a wrinkle, a curve or a streak.

Thus, in the last case the sector of permitted emphasis angles can change along the detectable defect. The speed of the adjustment can be parametrizable. The resolution of the sector of permitted emphasis angles is only based on the amount of device resources reserved for the representation of the angle.

On the other hand, an emphasis angle can be chosen from any direction of the web, according to which the earlier image data and/or the earlier filtered image data is weighted and however the earlier image data and/or the earlier filtered image data can be based on the local neighbourhood of the image data and/or filtered image data.

The weighting of the earlier image data and/or earlier filtered image data for creating filtered image data is independent or dependent on the earlier image data and/or earlier filtered image data and/or the side information data of the previous filter and/or the side information data of the previous filtering processes of the earlier image data and/or earlier filtered image data.

A set of preprocessing methods can be applied before creating a filtered image data. Selection of the preprocessing method is depending on the application. In addition to normal gray scale video signal, the source video signal for the method can be generated by utilizing high-pass, low-pass, band-pass or band-stop video filtering, pixel resolution modification, video signal reversal, true- or false-color image information or other information for weighting desired features of the original video signal to be detected with the method. For example, the traditional edge detection operators can be utilized before the creation of a filtered image data in the method, which is then used for integrating edge elements found by the edge detector.

Better detection performance is achieved if several variations of the invented method are utilized at the same time in series and/or in parallel. This is, naturally, depending on the available resources.

The web monitoring camera may be any type of electronic camera, for example a line scan camera or matrix camera. The image generated consists of k×n pixels, for example 1×1 or 4×4. The method allows defect searching for images having different resolutions by using preprocessing methods.

In an advantageous embodiment the method for processing image data in order to detect abnormalities in a web is performed using a computer. The programs to be used are stored in the memory of the computer or on computer readable media, which can be loaded on a computing device. These computer readable media have instructions for causing the computer to execute a method.

DETAILED DESCRIPTION

Figure 1:
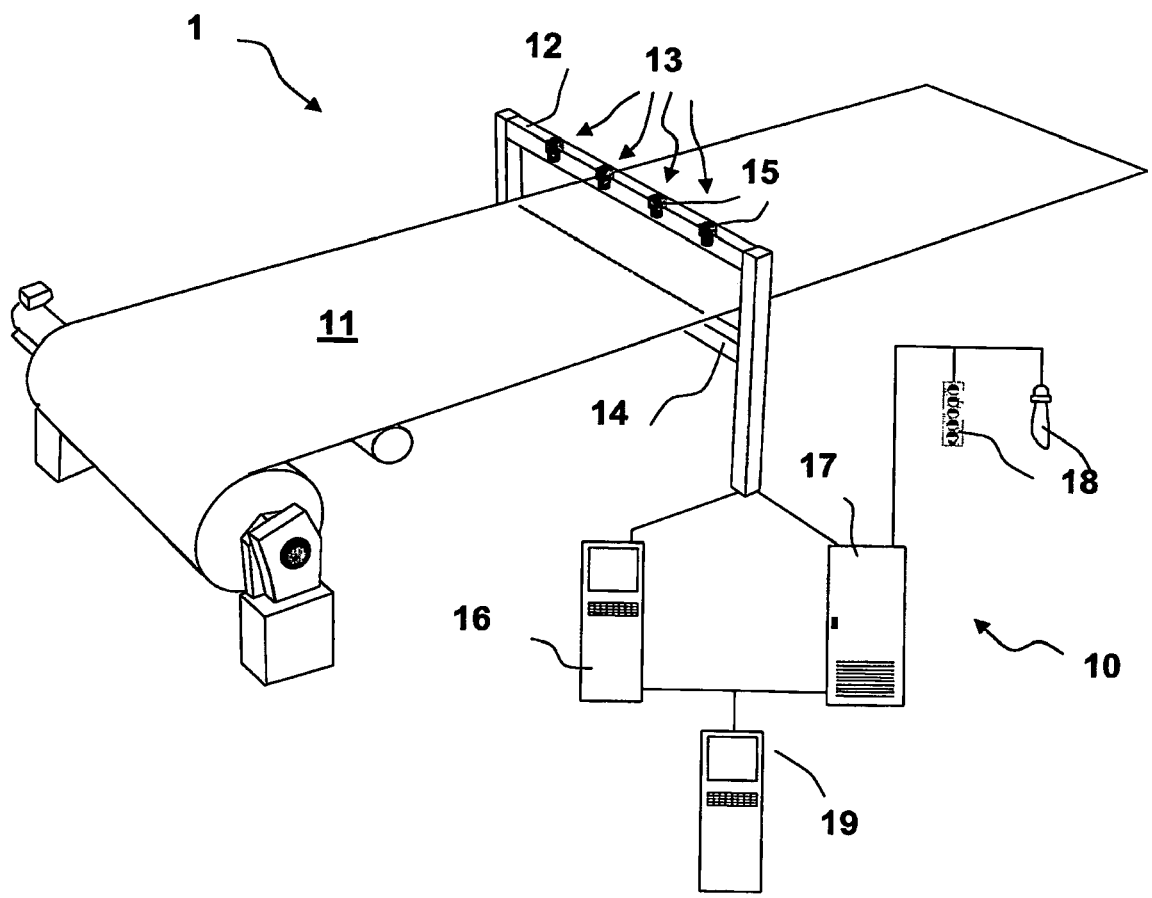
FIG. 1 is a schematic overview of a visual inspection system.

FIG. 1 illustrates an industrial application 1 of a visual inspection system 10, in connection of which the method and product for detecting abnormalities can be used. This is an example where the visual inspection system represents any visual system acquiring and collecting electronic images of various materials or objects for classifying different characteristics in them. Visual inspection system 10 may be applied for various continuous and discontinuous manufacturing lines. FIG. 1 illustrates a case in which the visual inspection system 10 is inspecting a moving and continuous web 11 manufactured on a process line such as a paper machine.

The moving web 11 is viewed by one or several cameras 13 from one side of the web 11. The cameras 13 are mounted on a suitable mechanical support such as a camera beam 12. The web 11 is illuminated from underneath by a light source 14. The light source may also be located above the web 11. Transmitting light, as illustrated in FIG. 1, is favorably used for translucent materials. Reflecting light is suitable especially for other types of materials. With the reflecting light, the illumination angle may either be specular or diffuse in respect to the camera-viewing angle.

The cameras 13 may be any types of electronic cameras, which can be directly or indirectly coupled to image-processing unit 15. Functions of the image-processing unit 15 may also be integrated with the camera 13, in which case the camera 13 is a more complicated and self-contained image-processing unit. Image data output of an analog camera, for example an analog CCD line scan camera or matrix camera, has to first be converted to digital format. Digital camera output is typically more ready for digital processing in the image-processing unit 15. The image-processing unit 15 receives from the cameras 13 a digital representation of the view imaged by the cameras 13. The representation is in the form of a series of digital numbers. Image processing unit 15 interprets this data as an electronic image, which is elsewhere referred to as an image, on the basis of the information it has about the properties of the camera 13. For example, the image processing unit 15 combines the successive series of data sent by a camera of line scan type to form a matrix that represents an image of the web 11.

The image-processing unit 15 is a separate, typically programmable, hardware unit. It can be partially or totally integrated with the camera, as depicted in FIG. 1. It can be also a personal computer or any other type of universal computer. One computer may take care of image data processing of one or several cameras. The method for processing image data is applied in this stage. The detection, i.e. obtaining an inspection signal that is recognized coming from a defect, is performed and by means of the method for processing image data the image of the web is divided into interesting regions. The outcome of this processing stage is a set of electronic images representing segmented parts of the web, the images being manipulated electronically to meet requirements of the application at hand.

The images are forwarded to the next processing step, which is image analysis. This step can be done in image-processing unit 15 or in a separate computer, which may be a part of an operator station 16 of the visual inspection system 10 and it is typically common to all the cameras 13. Image analysis comprises, for example, further segmentation of the interesting areas, such as defects, in the image. After segmentation, features describing properties of the regions found by segmentation can be extracted. The features are numeric values that will be used in recognizing the areas, i.e. in classifying them.

Operator station 16 contains the user interface of the visual inspection system 10. It is used for entering various tuning parameters and selecting desired displays and reports, which for example show the status of the system and the quality of the inspected products. Naturally the visual inspection system 10 requires separate means for supplying power to the system and devices for interfacing with the external systems such as the process itself. These means, which are well known to those of ordinary skill in the art, can be located in an electronic cabinet 17. In addition to operator station 16, external devices 18 can be used for alerting the operator.

The image data are stored in an image database. The image collection of the database consists of different types of digitized web defects. The defects are detected and their images are digitized from a running web. For classifying the defects a classifier 19 is used.

Digital line-scan cameras acquire the defect images with transmission or reflecting lighting and the images are stored to an image database together with a set of calculated features associated with certain areas of the image. A plurality of such defect images with a varying number of defects and associated features in each image form an image collection.

Figure 2:
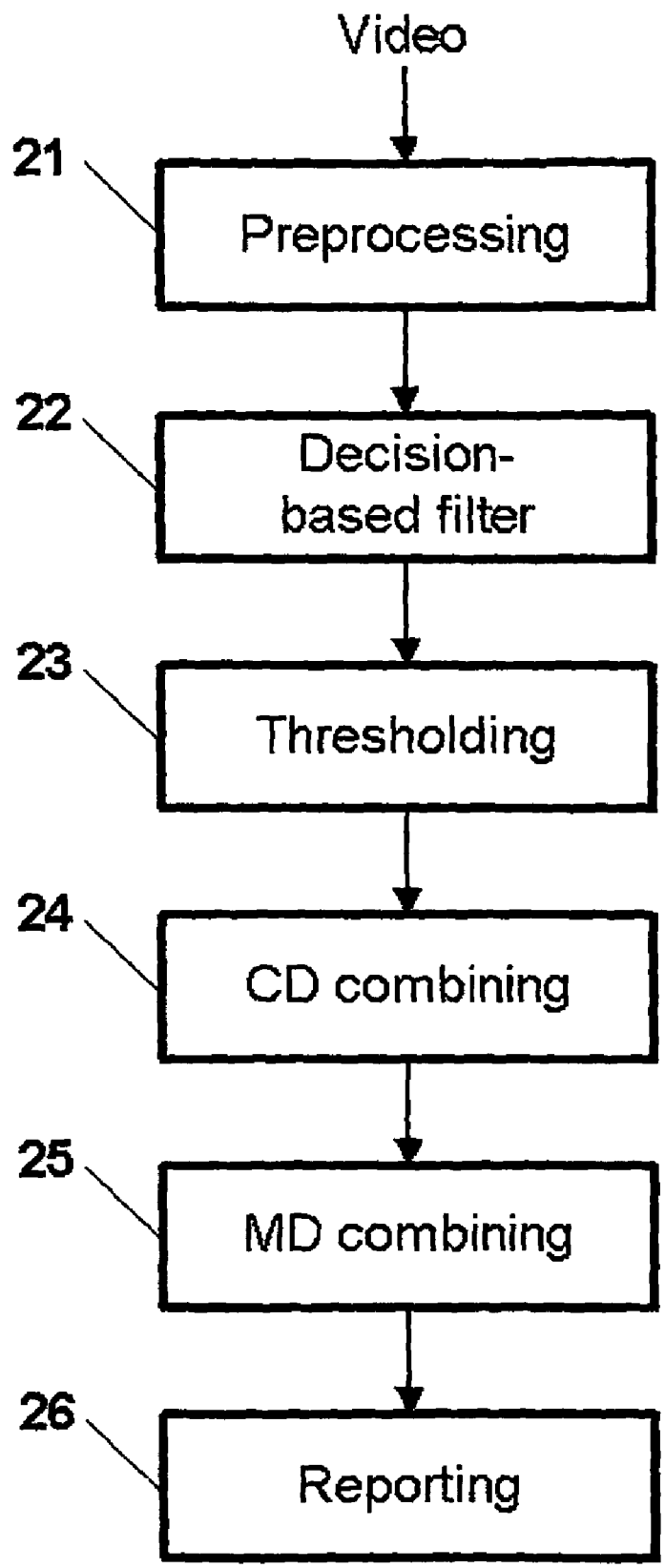
FIG. 2 presents a flow chart describing the main steps of the invention.

FIG. 2 presents a flow chart describing the main steps of the method. The method for processing image data in order to detect abnormalities in a web comprises of several steps numbered from 21 to 23 and is enhanced with steps 24-26.

Step 21 includes preprocessing methods for emphasizing desired properties of the original signal. Examples of preprocessing methods are saturation and cross direction and/or machine direction prefiltering. Depending on the case, the source video signal is either saturated (limited) or non-saturated before leading it to the decision-based filter 22. The saturation is used to point out weak defects comparing to the high contrast defects in intensity image. The source video signal, saturated or non-saturated, is prefiltered by a low-pass (for instance 2-dimension averaging), high-pass (for instance difference of adjacent pixels), bandpass, or band-stop, cross direction and/or machine direction filters or combinations of the previously mentioned filters. Cross direction and machine direction filtering are used to emphasize the high frequency or the low frequency weak features of defects in intensity or to emphasize the color image. This is essential for improving the S/N ratio where noise refers to the variations of the faultless product, for example the formation noise in paper. A low-pass filter is defined for example by a simple average filter, a Finite Impulse Response (FIR) filter or a median hybrid filter, which is a combination of average filters and median filters. A corresponding high-pass filter can be defined by the difference of the instant video value and the low-pass filtered value. The basic difference between an average and a median hybrid based filters is that the median hybrid filter filters edges out, but can see peaks quite ideally, while the average filter emphasizes both peaks and edges but peak response includes shadows. Shadows, however, may be a positive feature for some detection algorithms. Depending on the applied abnormalities detection method different preprocessing methods can be utilized allowing focusing to various defect types.

In a case of weak, elongated defects, where the original S/N ratio is equal or less than one, and the direction of the defect is unknown, the prefiltering in the cross direction or in the machine direction is required for defect detection. In a special case of long defects with a known direction, or in the case of short and strong defects, prefiltering can be skipped when Flat Field corrected video is used. Flat Field Correction applies a gain and offset correction per pixel to correct for illumination and sensor irregularities. The length of the defect defines the spatial frequency of the defect in the longitudinal direction of the defect. The length of the defect should be so long that a low-pass filter used for known direction integration can reduce the noise level enough to separate a defect signal from formation noise. The minimum length for detectable defects is based on the original S/N ratio, i.e. the longer the defect, the lower defect signal level is needed. For instance streak signals cannot be detected in most cases without a machine direction low-pass filtering because streak signals are so weak in comparison to the formation noise.

Figure 3:
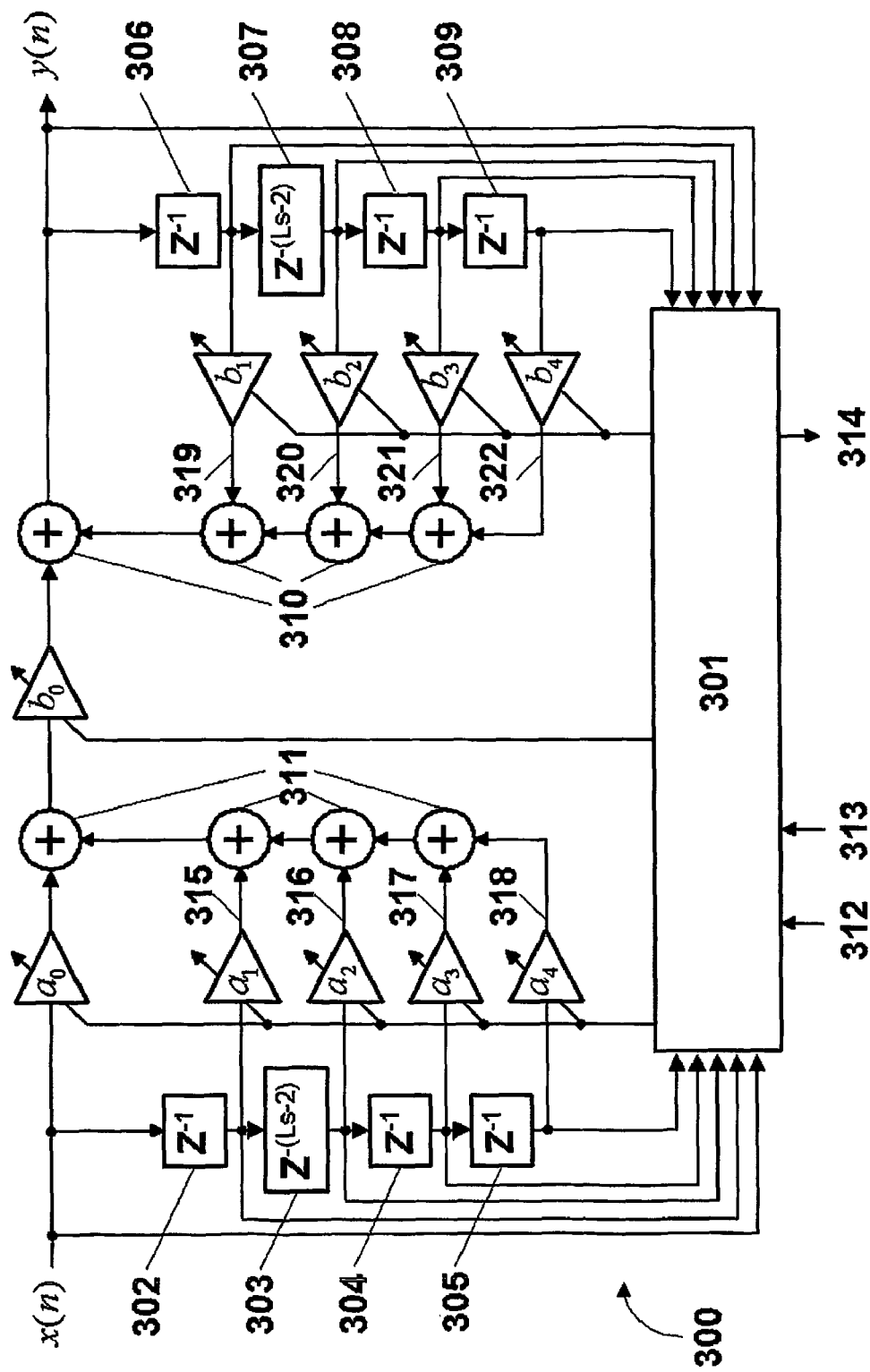
FIG. 3 is the internal structure of the decision-based filter system.

Filtering is performed in step 22. The decision-based filter utilizes the Infinite Impulse Response (IIR) filter structure and a nonlinear adaptive algorithm. The internal structure of the filter, where the direct form I realization of the IIR filter is used and where a nonlinear adaptive algorithm controls the filter coefficients, is shown in FIG. 3. Other realization structures of IIR filter like direct form II, transposed structures etc.

can be used as well. In the decision-based filter 300, the output video signal y(n), the filtered image data, can be given by $$y(n)=b_0(a_0(n)x(n)+a_1(n)x(n-1)+a_2(n)x(n-L_s+1)+a_3(n)x(n-L_s)+a_4(n)x(n-L_s-1))+b_1(n)y(n-1)+b_2(n)y(n-L_s+1)+b_3(n)y(n-L_s)+b_4(n)y(n-L_s-1),$$

where $a_0$-$a_4$ and $b_0$-$b_4$ are the filter coefficients controlled by the nonlinear adaptive algorithm 301, x(n) is the input video signal (image data), and $L_s$ is the length of an image line. The adders 310, 311 are shown in FIG. 3. The combining of the weighted image data and the weighted earlier image data and/or the weighted earlier filtered image data is performed by calculating a weighted sum of the values of earlier image data and/or earlier filtered image data and the input x(n). A two-dimensional local environment is established by video signal delay elements 306-309 for feedback part and 302-305 for forward part. If filter coefficients $a_1$-$a_4$ of forward part are set to zero, only earlier filtered image data i.e. the feedback part is considered. Correspondingly, if filter coefficients $b_1$-$b_4$ of feedback part are set to zero, only earlier image data, i.e., the forward part is considered and the filter structure corresponds to a Finite Impulse Response filter, FIR structure. Information like optional parameters 312 or optional side information from another filter 313 may be imported to the nonlinear adaptive algorithm 301 and also optional side information for another filter 314 exported. The nonlinear adaptive algorithm 301 controls the filtering 300. To implement a decision-based filter 300 only one image line of the earlier image data and one image line of the earlier filtered image data have to be buffered in the memory.

Figure 5:
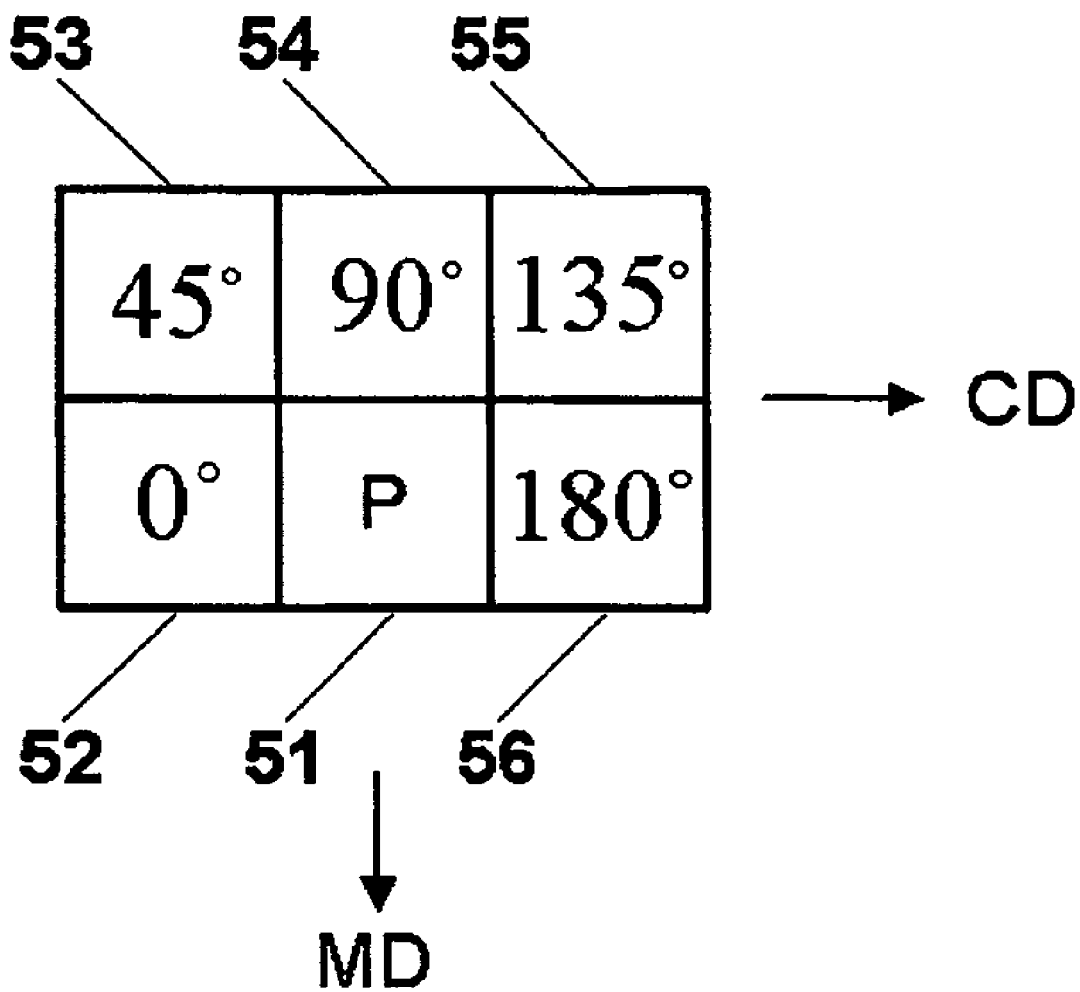
FIG. 5 shows an angle grid.

With a basic form of the decision-based filter, the defects in angles of 0-135° are covered. The emphasis angle grid is shown in FIG. 5. The local neighborhood of a pixel P 51 comprises of four pixel values: an angle 0° 52, an angle 45° 53, an angle 90° 54 and an angle 135° 55. The angle 0° 52 refers to the previous earlier image data value (forward part of the decision-based filter) or previous earlier filtered image data value (feedback part of the decision-based filter) from the current image line in a cross direction CD of the web. The three values in the angles of 45° 53, 90° 54 and 135° 55 are from the previous image line of the earlier image data (forward parts of the decision-based filter) or from the previous image line of the earlier filtered image data (feedback parts of the decision-based filter). The defects in the angles from 135° 55 to 180° 56 can be found by reversing the image data signal in cross direction before forwarding it to the decision-based filter. In that case one image line is stored in a memory and read from there in reversed order. If the whole emphasis angle range 0-180° should be covered, two decision-based filters can be used in parallel. MD refers to a machine direction.

For the sake of simplicity, the angle 0° refers to cross direction of the web and 90° to machine direction in the embodiments. However, the image data can be processed in any direction within the angle range. If, for instance, a pre-processing method rotates the image 90° then 0° in the calculation refers to MD and 90° in the calculation refers to CD.

Herein a pixel is supposed to be square. Actually, in most cases the pixel form and at the same time the real angle coverage is depending on the imaging geometry and the speed of the web, i.e. the pixel form is stretched in cross direction of the web or in machine direction.

Thresholding is made in step 23. The output of the decision-based filter (or filters), the filtered image data, is thresholded based on given detection levels to find curve or line defects.

In the following step 24 adjacent defect pixels in cross direction of the web are combined if the given distance limits is not exceeded. Adjacent defect areas in machine direction are combined if the given distance limit is not exceeded in step 25. At the end of the curve or line defect all defect attributes are reported 26 to the upper level of the detection system. Examples of defect attributes are: type of defect, positions of the minimum and maximum intensities of the defect, the boundaries of the defect, principal components and principal angle of the defect.

Figure 4:
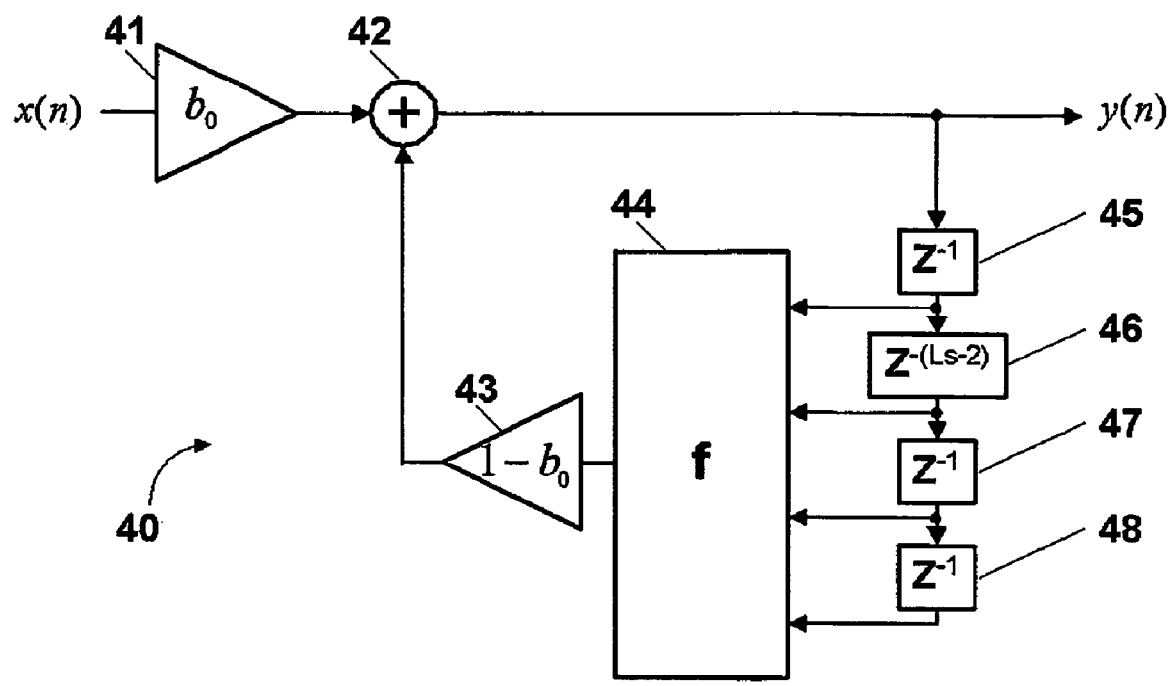
FIG. 4 is the internal structure of the filter system of the first embodiment.

In the first preferred embodiment the adaptive algorithm of the decision-based filter controls the feedback coefficients $b_1$-$b_4$ by utilizing minimum or maximum function. In this case the coefficients $a_1$-$a_4$ of the forward part are fixed set to zero and the coefficient $a_0$ is fixed set to 1. Minimum or maximum function is used to find minimum or maximum value of the earlier filtered image data and the corresponding $b_1$-$b_4$ coefficient is set to have value 1-$b_0$. Other $b_1$-$b_4$ coefficients are set to zero. In this way the IIR filter structure is reduced to the normalized first order IIR filter presented in FIG. 4. In the IIR filter 40 the output video signal y(n) can be given by $$y(n)=b_0x(n)+(1-b_0)f\{y(n-1),y(n-L_s+1),y(n-L_s),y(n-L_s-1)\},$$

where $b_0$ is the filter coefficient, x(n) is the input video signal, $f$ 42 is minimum or maximum function and $L_s$ is the length of a line. Thus, the new output y(n) is calculated as a weighted sum 41 of the old output, which is processed by a nonlinear feedback function 42, and the new input x(n). For instance, minimum function is used for dark defect detection and in proportion maximum function for light defect detection if low values correspond dark values in the intensity range. A two dimensional local environment is established by video signal delay elements Z 43-46. The filter coefficient $b_0$ controls the sensitivity of the detection. A longer defect, in machine direction, is needed for the lower defect signal levels, and, at the same time, a smaller filter coefficient value is needed.

This preferred embodiment is especially powerful for detecting weak, elongated defects appearing in angles of 0-135°. The usage of minimum and maximum functions inside the adaptive algorithm forms a method where the maximum intensity ridges or the minimum intensity valleys in the source video signal are followed and integrated the signal in the direction of the ridge or the valley. The preferred embodiment can also be utilized for weak area detection, where a weak area can be considered as a short and wide curve. The method integrates the signals in the highlands or in the lowlands of the weak areas. The strength of the method is based on the ability of spreading out over a weak area regardless of the shape or the size of the area.

In the second preferred embodiment a better S/N ratio compared to the first preferred embodiment is obtained by using parallel decision-based filters. In the definition of the minimum and the maximum values only two or three pixel values from the local neighborhood are taken into account. The permitted emphasis angles of the earlier filtered image data for creating the filtered image data are then fixed to a predetermined sector. This allows the filter to be focused to a desired search area defined by angles. The filters follow the ridges or the valleys in the angles of 0-45°, 45-90°, 90-135°, 0-90° or 45-135°. Parallel filters make possible to define different detection methods for different angle areas. The defects in the angles of 135-180° can be found by reversing the image data signal in cross direction before forwarding it to the decision-based filter. In that case one image line is stored in a memory and read from there in reversed order.

In the third preferred embodiment the decision-based filter is applied to detection of rippling streaks running nearly in the machine direction. The idea is to follow maximum or minimum intensity ridges or valleys in the source video signal and integrate the signal in the direction of the ridge or the valley. In this embodiment the sector of permitted emphasis angles can be narrowed from 45-135° to a narrow sector around 90°, for instance 82-98°. Real, physical emphasis angles are usually here closer to 90° because of normally in the streak detection systems the physical machine-directional pixel size is greater than the cross-directional pixel size.

In this embodiment the adaptive algorithm of the decision-based filter controls the feedback coefficients $b_2$-$b_4$ by utilizing minimum or maximum function i.e. the local neighborhood of a pixel comprises of three earlier filtered image data values in the angles of 45°, 90° and 135° from the previous image line. In this case the coefficients $a_1$-$a_4$ of the forward part and the coefficient $b_1$ of feedback part are fixed set to zero and the coefficient $a_0$ is fixed set to 1. Minimum or maximum function is used to find minimum or maximum value of the earlier filtered image data and the corresponding $b_2$-$b_4$ coefficient is set to have value $1$-$b_0$. Other $b_2$-$b_4$ coefficients are set to zero. This means the filter structure is reduced to the normalized first order IIR filter for which the feedback value is selected by utilizing minimum or maximum function. In the decision-based filter for rippling streak detection there is an additional side information data for informing the phase of the angle of the integration. This side information data is used to validate the earlier filtered image data values for maximum or minimum function. In each filtering step the local angle of the integration i.e. the angle of the value selected by utilizing the minimum or the maximum function is used to update the phase of the angle of the integration and this side information data is stored in a memory. There is a buffer reserved for the side information data. The length of the buffer is same as the length of one image line.

When a filtered image data value is calculated, an earlier filtered image data value from angles of 45° or 135° is permitted for minimum or maximum value calculation only if the corresponding angle phase value in the side information data is zero. If the minimum or maximum value of all permitted values is found from angles of 45° or 135°, the corresponding angle phase value is set to a fixed parameter value. The parameter defines the number of image lines required before permitting the emphasis angle of 45° or 135° again. The new angle phase value is positive for an angle of 45° and negative for an angle of 135°. If the minimum or the maximum value is found from the angle of 90°, the angle phase value is increased or decreased by one so that the new phase value approaches to zero. This means that every time the minimum or the maximum value is found from any other angle than 90°, the calculated filtered image data value can spread again to the same direction only after a parameterized number of scan lines. This constrains the decision-based filtering to a more narrow sector compared to the sector of permitted emphasis angles of 45-135°. In this case the permitted emphasis angles of the earlier filtered image data for creating the filtered image data are dependent on the previous emphasis angle of the earlier filtered image data.

In the fourth preferred embodiment, the adaptive algorithm of the decision-based filter includes side information data comprising several elements. The side information data comprise the global information updated during each filtering step and synchronized with the filtering result: 1. left angle area of the sector of permitted emphasis angles, 2. right angle area of the sector of permitted emphasis angles, 3. left angle of the sector of permitted emphasis angles, 4. right angle of the sector of permitted emphasis angles, 5. left transition phase and 6. right transition phase. The decision-based filter structure covers sector of permitted emphasis angles of 0-135°. The local neighborhood of a pixel comprises of four pixel values in the angles of 0° (current image line) and 45°, 90° and 135° (from the previous image line). The sector of permitted emphasis angles can be defined to be fixed or to adapt based on image data or some side information data. The sector of permitted emphasis angles is defined by giving the left and right angles of the sector, for example 63-100°. Left and right angles of the sector of permitted emphasis angles can be based on for example a fixed parameter or a side information data from another decision-based filter.

The whole angle range is divided to angle areas of 0-22.5°, 22.5-45°, 45-67.5°, 67.5-90°, 90-112.5° and 112.5-135°. These angle areas have corresponding primary angles of 0°, 45°, 45°, 90°, 90° and 135°. Furthermore, these angle areas have corresponding decision conditions of "at most", "at least", "at most", "at least", "at most" and "at least" for the left angle of the sector of permitted emphasis angles and "at least", "at most", "at least", "at most", "at least" and "at most" for the right angle of the sector of permitted emphasis angles. During each filtering step the earlier filtered image data values are validated for minimum or maximum value calculation. The validation is based on left and right transition phases, primary angles of the left and right angles of the sector of permitted emphasis angles, the corresponding decision conditions and left and right angles of the sector of permitted emphasis angles.

For example, if left angle of the sector of permitted emphasis angles is set to be 63° and the right angle of the sector of permitted emphasis angles is 100°, the corresponding angle areas are 45-67.5° and 90-112.5°, primary angles are 45° and 90° and the corresponding decision conditions are of type "at most" and "at least". This means the earlier filtered image data value in angle of 0° is never valid. The earlier filtered image data value in angle of 45° is valid if the left transition phase is at most the given limit i.e. the amount of sequential transitions from primary angle of 45° is at most the given limit. The limit in this case can be set to 1, which corresponds to the left angle of the sector of permitted emphasis angles of 63°. In this case the earlier filtered image data value in angle of 90° is always valid. The earlier filtered image data value in angle of 135° is valid if the right transition phase is at least the given limit i.e. the amount of sequential transitions from primary angle of 90° is at least the given limit. In this case the limit can be set to 6, which corresponds to the right angle of the sector of permitted emphasis angles of 100°.

The whole angle range of 0-180° is covered with two parallel decision-based filter structures where the output is the maximum or minimum of the decision-based filter outputs. Another decision-based filter is fed by reversed image line.

In the fifth preferred embodiment the adaptive algorithm of the decision-based filter includes a nonlinear function, the minimum or the maximum function. In this case a new side information data, comprising local and global angle of the defect, is updated and stored in a memory during each filtering step. The global angle is based on the local angle, which is defined by the emphasis angle of the earlier filtered image data value selected by utilizing minimum or maximum function. By low-pass filtering the local angle information a global angle can be calculated. The global angle describes the potential weak defect path as every pixel updates a path when progressing. The sector of permitted emphasis angles can then be defined, for example narrowed, based on the global angle information. This allows the emphasis to be focused to the found intensity ridge. The local and global angle side information can be forwarded to the next filtering stage, for example for a decision-based filter of the fourth embodiment, where the information can be used for definition of sector of permitted emphasis angles during each filtering step. When several defects are found at the same time, the global angle side information helps to follow each streak separately by focusing the emphasis to more narrow sectors. In particular, this is an important feature in the case where two or more defects are intersecting and there is a risk of mixing.

The sixth preferred embodiment is a preprocessing method for embodiments of 1-5. In this embodiment the forward part of the decision-based filter is used for preprocessing. For example by fixed setting the filter coefficients $a_0$-$a_4$ to have values $a_0=0$, $a_1=1$, $a_2=0$, $a_3=-1$ and $a_4=0$ the forward part is used for edge detector (focusing the angle of 45°) for the feedback part, which can then be used to integrate the edge elements. In another example by fixed setting the filter coefficients $a_0$-$a_4$ to have values $a_0=\frac{1}{5}$, $a_1=\frac{1}{5}$, $a_2=\frac{1}{5}$, $a_3=\frac{1}{5}$ and $a_4=\frac{1}{5}$ the forward part is used for local neighborhood averaging. In the third example the adaptive algorithm finds the maximum, minimum or median value from the earlier image data (four values) and the current image data value and set the corresponding filter coefficient of the forward part to be 1 and other $a_0$-$a_4$ coefficients are set to be zero. Then the maximum-, minimum- or median-filtered result is fed to the feedback part of the decision-based filter.

In the preferred seventh embodiment the decision-based filters are used in series. For instance, when two filters are used, the first filter is the decision-based filter described in the fifth preferred embodiment. It includes the side information comprising information of the local and global angles. It is used to determine the sector of permitted emphasis angles. The second filter may be the decision-based filter described in the fourth embodiment. In this case the adaptive algorithm of the filter utilizes the side information data from the first filter for defining sectors of permitted emphasis angles.

In the eighth preferred embodiment the whole angle range of 0-180° is covered with two parallel decision-based filter structures where the output is the maximum or the minimum of the decision-based filter outputs. Another decision-based filter is fed by reversed image data line.

In the ninth preferred embodiment the sector of permitted emphasis angles of the filter is steered by the earlier local angles. The controlling means are then the signal to be filtered, a potential defect and the angle of a potential defect.

In an advantageous embodiment the method is performed using a computer.

Various changes can be made to the invention without departing from the spirit thereof or scope.

The invention claimed is:

1. A method for processing image data in order to detect abnormalities in a web, wherein the web is monitored by at least one camera, whereby at least one image comprising of plurality of pixels is generated for creating the image data (x(n)), and the image data (x(n)) is stored in a memory, wherein the image data (x(n)) is filtered by a processor for creating a filtered image data (y(n)), wherein the current filtered image data (y(n)) is obtained by weighting the current image data (x(n), $a_0$, $b_0$) and at least one of image data (x(n)) from emphasis angles and filtered image data (y(n)) from emphasis angles; and by combining the obtained weighted current image data and the obtained at least one of weighted image data from emphasis angles and weighted filtered image data from emphasis angles, wherein the emphasis angles are dependent on the result of previous filtering; and wherein the filtering of the current image data (x(n)) is controlled by at least one nonlinear algorithm; and followed by thresholding the created filtered image data (y(n)).

2. A method according to claim 1, wherein the image data (x(n)) and/or filtered image data (y(n)) is weighted from any emphasis angle of 0°-135°.

3. A method according to claim 2, wherein the emphasis angle range of 0°-180° is covered with two parallel filters.

4. A method according to claim 1, wherein the image data (x(n)) and/or filtered image data (y(n)) is weighted from any emphasis angle of 0° or 45° or 90° or 135°.

5. A method according to claim 1, wherein the emphasis angle of the image data (x(n)) and/or filtered image data (y(n)) is independent from emphasis angles of previous filtering.

6. A method according to claim 1, wherein the emphasis angle of the image data (x(n)) and/or filtered image data (y(n)) is dependent on emphasis angles of previous filtering.

7. A method according to claim 1, wherein the emphasis angle of the image data (x(n)) and/or filtered image data (y(n)) is chosen from within a predetermined sector of permitted emphasis angles or is chosen from within the sector of permitted emphasis angles of previous filtering.

8. A method according to claim 1, wherein the emphasis angle of the image data (x(n)) and/or filtered image data (y(n)) is chosen from within a sector of permitted emphasis angles, and the sector is more narrow than the sector of permitted emphasis angles of previous filtering.

9. A method according to claim 1, wherein the image data (x(n)) and/or filtered image data (y(n)) is from the local neighbourhood of the current image data (x(n)) and/or current filtered image data (y(n)).

10. A method according to claim 1, wherein the filtering is weighted based on image data (x(n)) of previous filtering.

11. A method according to claim 1, wherein the filtering is weighted based on filtered image data (y(n)) of previous filtering.

12. A method according to claim 1, wherein the filtering is weighted based on at least one parameter.

13. A method according to claim 1, wherein the method further comprises utilizing of side information data and the side information data is stored in a memory.

14. A method according to claim 13, wherein the nonlinear adaptive algorithm includes side information data.

15. A method according to claim 13, wherein the filtering is controlled based on side information data from the previous stage of the filtering process.

16. A method according to claim 13, wherein the filtering is controlled based on side information data from another filter of the sequential and/or parallel and/or matrix filter structure.

17. A method according to claim 13, wherein side information data is created based on the image data (x(n)) and/or filtered image data (y(n)).

18. A method according to claim 13, wherein the side information data is created based on the side information data from the previous stages of filtering processes.

19. A method according to claim 13, wherein the side information data is created based on at least one parameter.

20. A method according to claim 13, wherein the side information data is created based on the side information data of previous filter.

21. A method according to claim 13, wherein the side information data is fixed to a predetermined value.

22. A method according to claim 13, wherein the side information data includes the direction of the image data (x(n)) from previous image data locations and/or the direction of the filtered image data (y(n)) from previous filtered image data locations.

23. A method according to claim 1, wherein the filtering is controlled based on a nonlinear adaptive algorithm utilizing at least one of maximum and minimum and median function.

24. A method according to claim 1, wherein the web monitoring camera is a line scan camera.

25. A method according to claim 1, wherein the web monitoring camera is a matrix camera.

26. A method according to claim 1, wherein the image is preprocessed before generating the image data (x(n)).

27. A method according to claim 26, wherein preprocessing rotates and/or reverses the image before generating the image data (x(n)).

28. A method according to claim 27, wherein preprocessing reverses the image in the cross direction of the web before generating the image data (x(n)).

29. A computer program product stored on computer readable medium for processing image data in order to detect abnormalities in a web, wherein the web is monitored by at least one camera, whereby at least one image comprising of plurality of pixels is generated for creating the image data (x(n)), and the image data (x(n)) is stored in a memory, that wherein the image data (x(n)) is filtered by a processor for creating a filtered image data (y(n)), wherein the current filtered image data (y(n)) is obtained by weighting the current image data (x(n), a0, b0) and at least one of image data (x(n)) from emphasis angles and filtered image data (y(n)) from emphasis angles; and by combining the obtained weighted current image data and the obtained at least one of weighted image data from emphasis angles and weighted filtered image data from emphasis angles wherein the emphasis angles are dependent on the result of previous filtering and wherein the filtering of the current image data (x(n)) is controlled by at least one nonlinear algorithm; and followed by thresholding the created filtered image data (y(n)).

* * * * *